US008556990B2

(12) United States Patent
Bartee et al.

(10) Patent No.: US 8,556,990 B2
(45) Date of Patent: Oct. 15, 2013

(54) REINFORCED PTFE MEDICAL BARRIERS (76) Inventors: Barry K. Bartee, Lubbock, TX (US);
Chaddick M. Bartee, Lubbock, TX (US)

(*) Notice: Subject to any disclaimer, the term of this patent is extended or adjusted under 35 U.S.C. 154(b) by 233 days.

(21) Appl. No.: 12/710,978

(22) Filed: Feb. 23, 2010

(65) Prior Publication Data
US 2010/0217392 A1 Aug. 26, 2010

Related U.S. Application Data (60) Provisional application No. 61/154,734, filed on Feb. 23, 2009.

(51) Int. Cl.
*A61F 2/02* (2006.01)
(52) U.S. Cl.
USPC .................................................. 623/23.72
(58) Field of Classification Search
USPC ........ 623/16.11, 18.11, 23.72–23.76; 606/60, 606/246, 248, 249, 280, 283–285, 907, 606/151; 424/422–426, 435; 433/215, 167, 433/175, 180–183, 229; 602/41–79; 428/158, 105
See application file for complete search history.

(56) References Cited

U.S. PATENT DOCUMENTS

| | | | | |
|---|---|---|---|---|
| 3,678,933 A | * | 7/1972 | Moore et al. | 604/366 |
| 3,699,958 A | * | 10/1972 | Szucs | 604/304 |
| 3,703,897 A | * | 11/1972 | Mack et al. | 602/43 |
| 3,715,265 A | * | 2/1973 | Allen et al. | 428/143 |
| 3,849,238 A | * | 11/1974 | Gould et al. | 602/46 |
| 4,060,081 A | * | 11/1977 | Yannas et al. | 623/15.12 |
| 4,077,410 A | * | 3/1978 | Butterworth et al. | 604/366 |
| 4,187,390 A | | 2/1980 | Gore | |
| 4,531,916 A | | 7/1985 | Scantlebury et al. | |
| 4,548,202 A | * | 10/1985 | Duncan | 606/220 |
| 4,610,250 A | * | 9/1986 | Green | 606/220 |
| 4,819,478 A | | 4/1989 | Melcher | |
| 4,849,285 A | | 7/1989 | Dillon | |
| 4,859,383 A | | 8/1989 | Dillon | |
| 4,923,471 A | * | 5/1990 | Morgan | 606/60 |

(Continued)

FOREIGN PATENT DOCUMENTS

| | | |
|---|---|---|
| EP | 0 574 091 A2 | 12/1993 |
| WO | 95/09583 | 4/1995 |

OTHER PUBLICATIONS

Vandana et al. "A Preliminary Study of the Guided Tissue Regeneration Procedures for Adjacent Buccal Root Coverage Using Single Gtam-Tr6t Membrane", Journal of clinical and Diagnostic Research, Feb. 2008, vol. 3, pp. 1365-1369.

(Continued)

*Primary Examiner* — Alvin J. Stewart
(74) *Attorney, Agent, or Firm* — Pillsbury Winthrop Shaw Pittman LLP (57) ABSTRACT

Systems, methods and devices usable in the repair of a bone defect are described. A portion of a bone defect is covered with a multilayered membrane that includes a reinforcing layer. A member of the reinforcing member is fastened to an area of bone and soft tissue is secured about the membrane. The membrane facilitates healing of the defect. One membrane comprises a plurality of layers that includes a binding layer and a PTFE layer which has a textured surface and a substantially smooth surface. The textured surface provides a top surface of the membrane and the substantially smooth surface contacts bone.

14 Claims, 6 Drawing Sheets

(56) References Cited

U.S. PATENT DOCUMENTS

| | | | |
|---|---|---|---|
| 4,948,651 A * | 8/1990 | DeBusk et al. | 428/110 |
| 5,017,830 A * | 5/1991 | Koike | 313/402 |
| 5,032,445 A | 7/1991 | Scantlebury et al. | |
| 5,093,179 A * | 3/1992 | Scantlebury et al. | 428/158 |
| 5,118,524 A | 6/1992 | Thompson et al. | |
| 5,171,148 A | 12/1992 | Wasserman et al. | |
| 5,196,016 A * | 3/1993 | Buser et al. | 606/86 R |
| 5,197,882 A * | 3/1993 | Jernberg | 433/215 |
| 5,264,214 A | 11/1993 | Rhee et al. | |
| 5,334,217 A * | 8/1994 | Das | 606/213 |
| 5,356,429 A | 10/1994 | Seare | |
| 5,356,432 A * | 10/1994 | Rutkow et al. | 623/23.72 |
| 5,360,341 A * | 11/1994 | Abramowitz | 433/215 |
| 5,366,460 A * | 11/1994 | Eberbach | 606/151 |
| 5,378,152 A * | 1/1995 | Elia | 433/173 |
| 5,405,394 A * | 4/1995 | Davidson | 623/18.11 |
| 5,441,508 A * | 8/1995 | Gazielly et al. | 606/151 |
| 5,443,483 A * | 8/1995 | Kirsch | 606/74 |
| 5,456,720 A * | 10/1995 | Schultz et al. | 623/23.64 |
| 5,458,636 A * | 10/1995 | Brancato | 623/23.72 |
| 5,480,711 A * | 1/1996 | Ruefer | 428/315.5 |
| 5,496,359 A * | 3/1996 | Davidson | 607/115 |
| 5,501,661 A * | 3/1996 | Cartmell et al. | 602/58 |
| 5,511,565 A | 4/1996 | Syers | |
| 5,545,226 A | 8/1996 | Wingo et al. | |
| 5,588,443 A * | 12/1996 | Davidson | 600/585 |
| 5,593,441 A * | 1/1997 | Lichtenstein et al. | 600/37 |
| 5,607,689 A | 3/1997 | Checchi | |
| 5,611,347 A * | 3/1997 | Davidson | 600/510 |
| 5,628,790 A * | 5/1997 | Davidson et al. | 623/2.36 |
| 5,632,779 A * | 5/1997 | Davidson | 623/1.51 |
| 5,647,858 A * | 7/1997 | Davidson | 604/264 |
| 5,649,951 A * | 7/1997 | Davidson | 606/198 |
| 5,700,479 A | 12/1997 | Lundgren | |
| 5,716,408 A * | 2/1998 | Eldridge et al. | 606/213 |
| 5,798,117 A | 8/1998 | New et al. | |
| 5,957,690 A | 9/1999 | Bartee et al. | |
| 5,993,972 A | 11/1999 | Reich et al. | |
| 6,019,764 A | 2/2000 | Bartee | |
| 6,022,553 A | 2/2000 | Anders et al. | |
| 6,042,534 A * | 3/2000 | Gellman et al. | 600/30 |
| 6,080,194 A * | 6/2000 | Pachence et al. | 623/23.76 |
| 6,093,201 A * | 7/2000 | Cooper et al. | 606/232 |
| 6,113,623 A * | 9/2000 | Sgro | 606/215 |
| 6,123,709 A * | 9/2000 | Jones | 606/281 |
| 6,171,329 B1 * | 1/2001 | Shaw et al. | 606/213 |
| 6,206,907 B1 * | 3/2001 | Marino et al. | 606/215 |
| 6,224,630 B1 * | 5/2001 | Bao et al. | 623/17.16 |
| 6,241,768 B1 * | 6/2001 | Agarwal et al. | 623/11.11 |
| 6,258,124 B1 * | 7/2001 | Darois et al. | 623/14.13 |
| 6,290,708 B1 * | 9/2001 | Kugel et al. | 606/151 |
| 6,302,897 B1 * | 10/2001 | Rousseau | 606/190 |
| 6,319,264 B1 * | 11/2001 | Tormala et al. | 606/151 |
| 6,325,627 B1 | 12/2001 | Ashman | |
| 6,328,765 B1 * | 12/2001 | Hardwick et al. | 623/23.72 |
| 6,332,779 B1 * | 12/2001 | Boyce et al. | 433/215 |
| 6,383,201 B1 * | 5/2002 | Dong | 606/151 |
| 6,394,807 B2 * | 5/2002 | Robinson | 433/173 |
| 6,409,764 B1 * | 6/2002 | White et al. | 623/16.11 |
| 6,451,032 B1 * | 9/2002 | Ory et al. | 606/151 |
| 6,464,709 B1 * | 10/2002 | Shennib et al. | 606/155 |
| 6,497,650 B1 * | 12/2002 | Nicolo | 600/37 |
| 6,592,622 B1 * | 7/2003 | Ferguson | 623/13.14 |
| 6,712,859 B2 * | 3/2004 | Rousseau et al. | 623/23.64 |
| 6,736,854 B2 * | 5/2004 | Vadurro et al. | 623/23.72 |
| 7,258,700 B2 * | 8/2007 | Lambrecht et al. | 623/17.16 |
| 7,547,319 B2 * | 6/2009 | Segal et al. | 606/279 |
| 7,651,769 B2 * | 1/2010 | Dubrow | 428/371 |
| 7,682,540 B2 * | 3/2010 | Boyan et al. | 264/212 |
| 7,789,888 B2 * | 9/2010 | Bartee et al. | 606/151 |
| 7,806,911 B2 * | 10/2010 | Peckham | 606/248 |
| 7,824,420 B2 * | 11/2010 | Eldridge et al. | 606/151 |
| 7,887,593 B2 * | 2/2011 | McKay et al. | 623/17.16 |
| 7,901,461 B2 * | 3/2011 | Harmon et al. | 623/23.72 |
| 7,959,554 B2 * | 6/2011 | McAlexander et al. | 600/37 |
| 7,972,360 B2 * | 7/2011 | Dean | 606/215 |
| 7,981,022 B2 * | 7/2011 | Gellman et al. | 600/30 |
| 8,012,205 B2 * | 9/2011 | Plouhar et al. | 623/13.17 |
| 8,029,286 B2 * | 10/2011 | Craig et al. | 433/228.1 |
| 8,052,753 B2 * | 11/2011 | Melvin | 623/13.14 |
| 2002/0123750 A1 * | 9/2002 | Eisermann et al. | 606/69 |
| 2003/0100898 A1 * | 5/2003 | Wellisz | 606/69 |
| 2003/0105530 A1 * | 6/2003 | Pirhonen et al. | 623/23.72 |
| 2003/0216669 A1 * | 11/2003 | Lang et al. | 600/587 |
| 2004/0059418 A1 * | 3/2004 | McKay et al. | 623/17.16 |
| 2004/0224182 A1 * | 11/2004 | Lazarev | 428/690 |
| 2004/0232406 A1 * | 11/2004 | Weiss et al. | 257/35 |
| 2004/0260340 A1 * | 12/2004 | Jacobs et al. | 606/213 |
| 2005/0015088 A1 * | 1/2005 | Ringeisen | 606/69 |
| 2005/0023603 A1 * | 2/2005 | Eldridge et al. | 257/315 |
| 2005/0079200 A1 * | 4/2005 | Rathenow et al. | 424/423 |
| 2005/0083047 A1 * | 4/2005 | Lee et al. | 324/210 |
| 2005/0102036 A1 | 5/2005 | Bartee et al. | |
| 2005/0164045 A1 * | 7/2005 | Rothbrust et al. | 428/701 |
| 2005/0177162 A1 * | 8/2005 | McLeod et al. | 606/70 |
| 2006/0200140 A1 * | 9/2006 | Lange | 606/61 |
| 2006/0224242 A1 | 10/2006 | Swords et al. | |
| 2007/0061015 A1 | 3/2007 | Jensen et al. | |
| 2007/0129811 A1 * | 6/2007 | Plouhar et al. | 623/23.75 |
| 2009/0076541 A1 * | 3/2009 | Chin et al. | 606/215 |
| 2009/0286205 A1 * | 11/2009 | Johnson et al. | 433/222.1 |
| 2010/0249947 A1 * | 9/2010 | Lesh et al. | 623/23.74 |
| 2010/0312357 A1 * | 12/2010 | Levin et al. | 623/23.72 |
| 2011/0118844 A1 * | 5/2011 | Lambrecht | 623/17.16 |
| 2011/0250565 A1 * | 10/2011 | Yarovesky | 433/199.1 |
| 2011/0264119 A1 * | 10/2011 | Bayon et al. | 606/151 |
| 2011/0264120 A1 * | 10/2011 | Bayon et al. | 606/151 |
| 2011/0270284 A1 * | 11/2011 | Beauchamp et al. | 606/151 |
| 2011/0288567 A1 * | 11/2011 | Ranucci et al. | 606/151 |
| 2011/0295283 A1 * | 12/2011 | Darois et al. | 606/151 |
| 2013/0035704 A1 * | 2/2013 | Dudai | 606/151 |

OTHER PUBLICATIONS

Wilson et al. "Advances in the Use of Guided Tissue Regeneration for Localized Ridge Augumentation in Combination with Dental Implants", Texas Dental Journal, Jul. 1994, vol. 5, pp. 7-10.

Buser et al. "Regeneration and Enlargement of Jaw Bone Using Guided Tissue Regeneration", Clin. Oral Impl. Res., 1990, vol. 1, pp. 22-32.

Scantlebury, Todd V., "1982-1992: A Decade of Technology Development for Guided Tissue Regeneration", J. Periodontol, 1993, vol. 64, pp. 1129-1137.

International Search Report, PCT/US2010/025093, Apr. 22, 2010.

* cited by examiner

FIG-1

Textured Surface

FIG-2

Untextured Surface

BUCCAL

REINFORCED PTFE MEDICAL BARRIERS

CROSS-REFERENCE TO RELATED APPLICATIONS

The present Application claims priority from U.S. Provisional Patent Application No. 61/154,734, filed Feb. 23, 2009, which application is incorporated herein by reference for all purposes.

The present Application is related to copending U.S. patent application Ser. No. 11/941,060 entitled "Hydrophilic High Density PTFE Medical Barrier," filed Nov. 15, 2007 which is a continuation of U.S. patent application Ser. No. 10/947,066, filed Sep. 21, 2004, which issued as U.S. Pat. No. 7,296,998 and U.S. patent application Ser. No. 08/971,390, filed Nov. 17, 1997 entitled "Textured High Density PTFE Medical Barrier," which issued as U.S. Pat. No. 5,957,690, each related application being expressly incorporated by reference herein.

BACKGROUND OF THE INVENTION

1. Field of the Invention

The present invention relates generally to repair of bone defects and more particularly, to systems, apparatus and methods of assisting growth of bone and tissue after trauma and surgery.

2. Description of Related Art

Regeneration of bone defects remains a significant clinical problem. For example, in oral reconstructive surgery, bone defects may occur as a result of tooth extraction, cyst formation, surgery, trauma, or destruction by periodontal or peri-implant disease. Some synthetic membrane materials have been used for guided tissue regeneration, including cellulose acetate filter, perforated Teflon®, mantle leaf, expanded polytetrafluoroethylene (PTFE), and resorbable polymers. Naturally derived membranes such as bovine collagen and lyophilized dura mater have also been used.

Membrane-assisted guided tissue regeneration techniques are based on the hypothesis that during wound healing, cells adjacent to the bone defect migrate to repopulate the defect at various rates. By placing a barrier such as a biocompatible membrane over the defect, the rapidly migrating connective tissue cells will be mechanically prevented from entering the defect. Theoretically, this allows the slower-migrating mesenchymal cells from the surrounding bone and marrow, having osteogenic potential, to repopulate the defect selectively.

A common feature of earlier synthetic membrane systems is macroporosity, which was believed to enhance regeneration by improving wound stability through tissue integration and allowing diffusion of extra-cellular nutrients across the membrane. However, in some applications, the use of macroporous biomaterials in the oral cavity can result in early bacterial contamination of the material. Bacterial contamination of macroporous biomaterials can result in antibiotic-resistant infection, which can require early removal of the device.

Additionally, a common feature of macroporous biomaterials is the ingrowth of surrounding tissues, which was thought to be necessary for stabilization of the implant. In macroporous biomaterials, cells readily incorporate into the material and connective tissue is manufactured. While this incorporation into the material slows the migration of cells, it presents a difficult problem to the patient and the surgeon during the removal process. The incorporated cells and fibrous connective material may make removal of the barrier painful and traumatic to the patient and very time consuming and difficult for the surgeon.

It has been discovered that the use of a flexible high-density polytetrafluoroethylene (PTFE) sheet material is useful in guided tissue regeneration. High density PTFE is substantially nonporous or microporous so as not to incorporate cells or attach to fibrous adhesions. By presenting a smooth surface to the biological materials, a high density PTFE barrier is easily inserted and removed following extended implantation periods. An example of a high density PTFE barrier material is disclosed in U.S. Pat. No. 5,480,711.

While high density PTFE medical barriers provide advantages over macroporous barriers, the smooth surface of the high density PTFE barriers sometimes leads to dehiscence of the soft tissue overlying the barrier. The dehiscence problem is caused by the fact that the smooth surface of high density PTFE will not incorporate cells and will not attach to fibrous adhesions. Thus, over the course of healing, the incision will occasionally split open over the high density PTFE barrier.

BRIEF SUMMARY OF THE INVENTION

Certain embodiments of the invention comprise systems and methods for repairing bone defects that can include covering a portion of a bone defect using a reinforced membrane and securing soft tissue about the membrane, whereby the membrane facilitates healing of the defect. In certain embodiments, the membrane may comprise a plurality of layers, including a binding layer and a polytetraflouroethylene polymer (PTFE) layer, the PTFE layer having a textured surface and a substantially smooth surface. In certain embodiments, the textured surface provides a top surface of the membrane. In certain embodiments, the substantially smooth surface contacts the bone. In certain embodiments, the textured surface is made of unsintered PTFE. In certain embodiments, the substantially smooth surface is made of expanded PTFE. In certain embodiments, the binding layer is a titanium binder.

Certain embodiments of the invention provide a medical barrier that includes a reinforced material which is a titanium binder configured to span a bone cavity and adapted for fixation to bone surrounding the bone cavity and a PTFE membrane attached at one or more points to the titanium binder, with the titanium binder having one or more elongate members; wherein the titanium binder can be formed in a desired shape and/or deformed to obtain the desired shape. In certain embodiments, the elongate members have one or more predrilled holes suitable for securing a fastener to an area of bone. In certain embodiments, the fastener is a surgical screw. In certain embodiments, the fastener is a surgical pin. In certain embodiments, at least one of the elongate members is free to move independently of the PTFE membrane. In certain embodiments, the PTFE membrane is attached to a portion of a bottom layer of the PTFE membrane.

Certain embodiments provide a medical barrier that includes a sheet of unsintered substantially unexpanded polytetrafluoroethylene (PTFE) polymer material having a density in a range of about 1.2 gm/cc to about 2.3 gm/cc, and preferably in the range of about 1.45 gm/cc to about 1.55 gm/cc, and having at least one textured surface. Preferably, the sheet has one textured surface and one substantially smooth surface, and has substantially uniform strength in all directions.

In certain embodiments, the sheet of the medical barrier has a thickness in a range of about 0.125 mm to about 0.25 mm. The textured surface can be formed by a plurality of indentations formed in the surface of the sheet. The indentations can have a depth less than the thickness of the sheet and each indentation can have a preferred width of about 0.5 mm. The indentations can be distributed substantially uniformly over the surface of the sheet. In certain embodiments, the indentations are distributed over the surface of the sheet at about 196 indentations per square centimeter.

The medical barrier of the present invention can be particularly well adapted for use in guided tissue regeneration in the repair of bone defects, and particularly in the repair of alveolar bone defects. The barrier prevents the entry of rapidly migrating gingival tissue cells into the defect and allows the alveolar bone to regenerate. During healing, the gingival tissue adheres somewhat to the textured surface of the barrier to anchor the gingival tissue over the barrier, thereby preventing dehiscence or splitting open of the tissue covering the material. However, the high density unexpanded substantially non-porous nature of the medical barrier of the present invention can prevent gingival tissue from growing into or through the barrier and the barrier may be removed with a minimum of trauma to the gingival tissue after the bone defect has healed.

DETAILED DESCRIPTION OF THE INVENTION

Embodiments of the present invention will now be described in detail with reference to the drawings, which are provided as illustrative examples so as to enable those skilled in the art to practice the invention. Notably, the figures and examples below are not meant to limit the scope of the present invention to a single embodiment, but other embodiments are possible by way of interchange of some or all of the described or illustrated elements. Wherever convenient, the same reference numbers will be used throughout the drawings to refer to same or like parts. Where certain elements of these embodiments can be partially or fully implemented using known components, only those portions of such known components that are necessary for an understanding of the present invention will be described, and detailed descriptions of other portions of such known components will be omitted so as not to obscure the invention. In the present specification, an embodiment showing a singular component should not be considered limiting; rather, the invention is intended to encompass other embodiments including a plurality of the same component, and vice-versa, unless explicitly stated otherwise herein. Moreover, applicants do not intend for any term in the specification or claims to be ascribed an uncommon or special meaning unless explicitly set forth as such. Further, the present invention encompasses present and future known equivalents to the components referred to herein by way of illustration.

The term sintered is a term well known in the art and is used herein consistent with that understanding. The term unsintered is used herein to describe PTFE polymer that has not been subjected to the sintering process. Unsintered PTFE is substantially unexpanded and typically contains no substantially defined internodal distance, which substantially reduces its porosity relative to e-PTFE. The limited porosity of the unsintered, substantially unexpanded d-PTFE substantially reduces tissue adhesions to the d-PTFE or migration of tissue into the d-PTFE. However, the limited porosity allows for the passage of ions and other small molecules necessary for cellular nourishment and waste transport.

Figure 1:
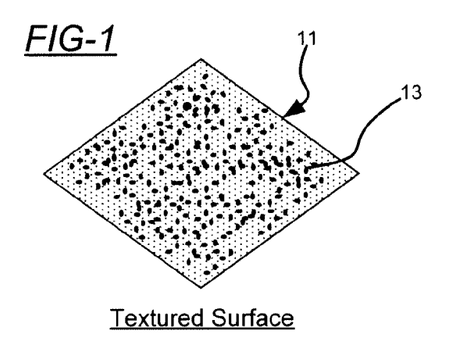
FIG. 1 is a perspective view showing the textured surface of the medical barrier of the present invention.
Figure 2:
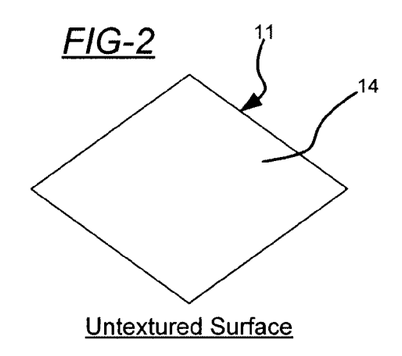
FIG. 2 is a perspective view showing the untextured surface of the medical barrier of the present invention.
Figure 3:
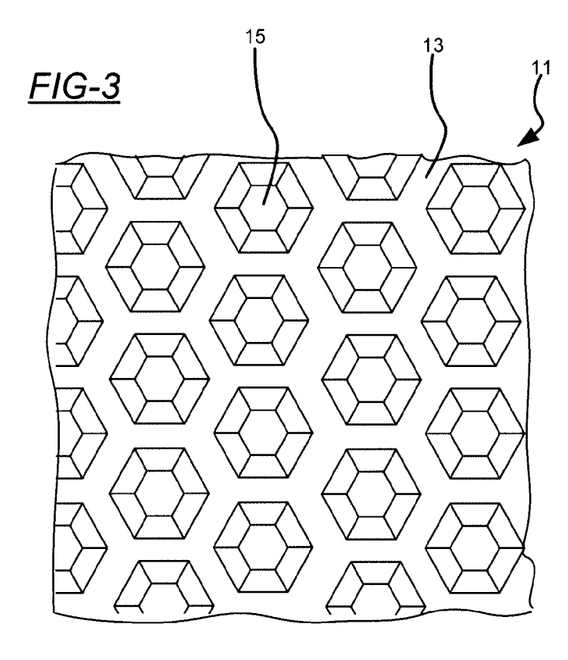
FIG. 3 is an enlarged view of the textured surface of the medical barrier of the present invention.

Certain aspects of the invention will be described with reference to the example depicted in FIGS. 1 and 2. Certain embodiments of the invention employ a medical barrier 11. Barrier 11 may comprise a sheet of unsintered substantially unexpanded polytetrafluoroethylene (PTFE) polymer. Barrier 11 includes a textured surface 13 and an untextured surface 14. In one example, barrier 11 has a sheet thickness in the range of about 0.125 mm to about 0.25 mm and a density in the range of about 1.2 gm/cc to about 2.3 gm/cc. In another example, the density lies in the range of about 1.45 gm/cc to about 1.55 gm/cc. With reference to FIG. 3, the textured surface can be formed by a plurality of indentations 15 formed in surface 13 of barrier 11. Indentations 15 may be hexagonal in shape, although other shapes are contemplated and fall within the scope of the invention. The indentations can have a depth less than the thickness of the sheet and, in certain embodiments, indentations 15 can be about 0.15 mm deep. The indentations 15 may be dimensioned based on application and the width can be greater or smaller, including for example, dimensions of about 0.5 mm wide.

The distribution of indentations 15 can be substantially uniform over surface 13 of barrier 11. In one example, approximately 150 indentations are provided per square centimeter over surface 13 of sheet 11. In another example 250 indentations are provided per square centimeter over surface 13 of sheet 11.

Figure 4:
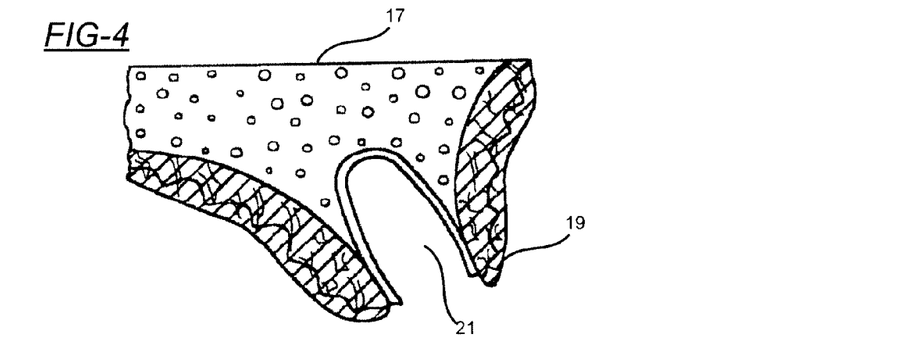
FIG. 4 is a lateral cross-sectional view of a maxillary bony defect resulting from the extraction of a tooth.
Figure 5:
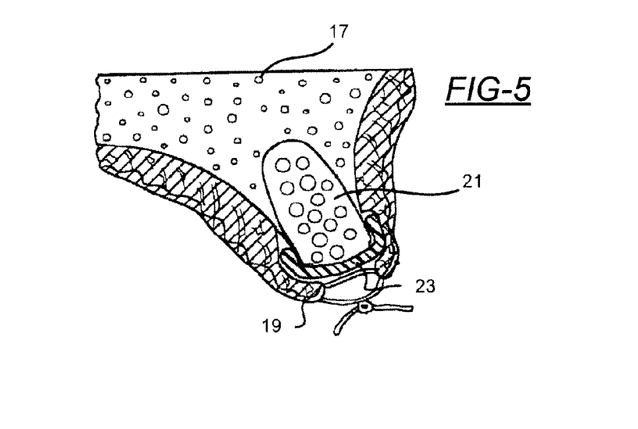
FIG. 5 is a lateral cross-sectional view of the maxillary bony defect of FIG. 4 showing the placement of the medical barrier of the present invention to cover the bony defect with the mucoperiosteal flap sutured over the medical barrier.
Figure 6:
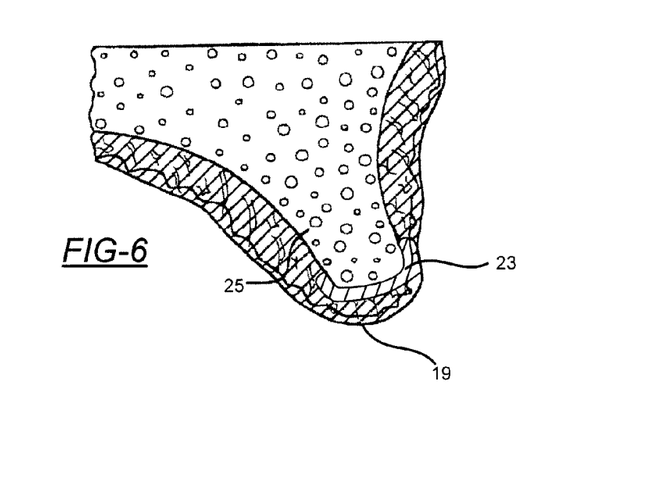
FIG. 6 is a lateral cross-sectional view showing the healed maxillary bony defect of FIG. 4 with the gingival tissue healed over the medical barrier of the present invention.

FIGS. 4-6, show an example of the manner of use of the barrier of the present invention. FIG. 4 is a lateral cross-sectional view of an adult human maxilla after a tooth extraction showing the bone of the alveolar process 17. Soft tissue gingiva 19 covers bone 17. A tooth socket 21 provides an example of a bone defect. Other examples of bone defects are those caused by periodontal disease, cyst formation, surgery, or trauma. Normal healing of a defect includes migration of foreign cells such as fibroblasts and gingival epithelial cells. As the cells proliferate into the defect, they inhibit bone cell regeneration, which results in overall loss of bone mass. In the case of extractions, the loss of bone mass results in a loss of alveolar ridge profile.

FIG. 5 is an example of a method for using the barrier of the present invention. Socket 19 is packed with granular particles of hydroxyapatite as a precursor to bone. Other materials and/or articles, such as endosseous type dental implants, may be placed into socket 21. The packed socket 21 can be covered with a layer 23 of the barrier of the present invention. The smooth side of the barrier can be placed over socket 21 and bone 17. Thus, the textured side of the barrier can be positioned adjacent the gingival tissue 19. The material provides substantially uniform strength in all directions, thereby allowing the surgeon to shape layer 23 over socket 21 and bone 17. After layer 23 is placed over socket 21 and bone 17, the gingival flaps 19 are sutured over layer 23. Layer 23 holds the hydroxyapatite particles in place in socket 21 during healing and prevents migration of cells and connective tissue into socket 21. However, connective tissue typically forms a weak attachment with the textured surface of layer 23, without growing through the material. The attachment is weak enough that the layer may be removed after healing without significant trauma but is strong enough to prevent the dehiscence.

FIG. 6 shows a typical extraction site after healing, but prior to removal of layer 23. As shown in FIG. 6, the alveolar ridge profile 25 can be preserved and the gingival tissue 19 can be completely healed over ridge 25. Layer 23 may be removed by making a small incision (not shown) in gingival tissue 19 to expose a portion of layer 23. The layer 23 may then be pulled out with forceps or the like. The material can typically be easily pulled out without trauma to the patient because the attachment of the connective tissue to the textured surface is typically weak.

In certain embodiments, a multilayer reinforced material configured to span a bone cavity and adapted for fixation to bone surrounding the bone cavity can be used. The multilayer material can comprise various materials forming one or more layers to provide qualities such as: strength in substantially all directions, inertness, pliability, malleability, resistance to compressive forces, and adhesiveness, such that the materials used to form each layer can be selected to impart different functional capabilities. For example, the layers can optionally be made of PTFE, such as expanded PTFE, unsintered PTFE, high density PTFE, which typically provide strength, flexibility and inertness. In certain embodiments, a titanium binder forms a layer of the multi-layered material. The titanium binder is typically bendable and can have one or more elongate members such that the titanium binder can be formed to obtain a desired shape and/or can be deformed, reformed to obtain the desired shape prior to placement about the bone defect and maintain the formed shape upon placement. In one example, portions or all of the binder can be bent, twisted and/or stretched as necessary to obtain the desired shape. In certain embodiments, other malleable or flexible inert materials can be used to form a binding layer. The titanium binding layer typically has one or more holes suitable for securing a fastener such as a surgical pin or screw to the bone repair site. In certain embodiments, the fastener secures the multilayered reinforced material to the surgical site.

In certain embodiments, layers of the multilayered reinforced material can be attached at one or more points. The layers may be fixed or attached using any suitable means, including use of an adhesive layer for attachment or bonding the layers. The PTFE layers partially cover the titanium binder. According to certain aspects of the invention, the PTFE layers can substantially envelope the titanium binder. Certain embodiments can include a bi-layered titanium reinforced material, as described in more detail below.

Figure 7:
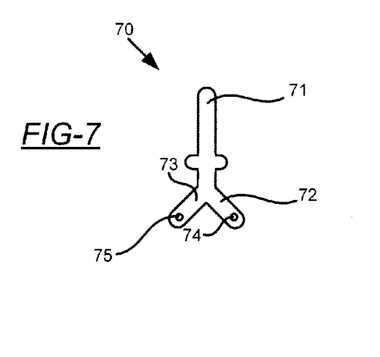
FIG. 7 depicts a first example of a titanium reinforcement binder.

FIG. 7 shows an example of a titanium reinforcement binder for use in the bi-layered titanium reinforced membrane of FIG. 8 (described below). In certain embodiments, the titanium reinforcement binder has a frame 70 or body suitable for placement over a bone cavity, such as an alveolar cavity. The frame 70 which can have a first elongate member 71, for placement over the cavity toward a lingual side of the cavity, and two elongate members 72 and 73 in a "Y-shaped configuration" at an opposite end of the titanium binder, each having perforations or holes 74 and 75 for securing a fastener, such as a surgical screw to an area of bone, typically at a surgical site, for example on the buccal side of the jaw, or upper alveolar arch, in the repair of alveolar defects or maxillofacial defects.

In the example of FIG. 7, dimensions of the binder are selected based on the application. Similarly, the physical and mechanical properties of the binder are selected according to application. In the depicted examples, surgical grade titanium is used to provide malleability, strength and low weight. It will be appreciated that Titanium possesses strength and weight characteristics that, together with the biologically inert nature of the metal offers advantages in many applications. It is contemplated that some applications may indicate that other dimensions, ratios of dimensions and materials may be employed. For example, repair of bone material in a pelvis or hip may require the use of steel or other materials.

The structural configuration of the binder may be selected as desired to facilitate ease of placement and use in reconstructive repair of bone defects of various sizes, related soft tissue repair or skeletal surgery. The structural configuration of the binder can be selected to provide one or more appendages, or elongate members, suitable for placement about bone or surrounding tissues. The overall shape of the binder may be selected to achieve a desired strength, load distribution, barrier support, placement of fasteners, comfort, ease of insertion and/or removal and so on. The binder can also comprise bendable non-toxic materials. Moreover, certain embodiments employ materials coated, layered or encased in non-toxic materials. Binders can comprise titanium, stainless steel, platinum, ceramics, composites, carbon fiber materials and customized micro- or nano-material-based materials.

Figure 8:
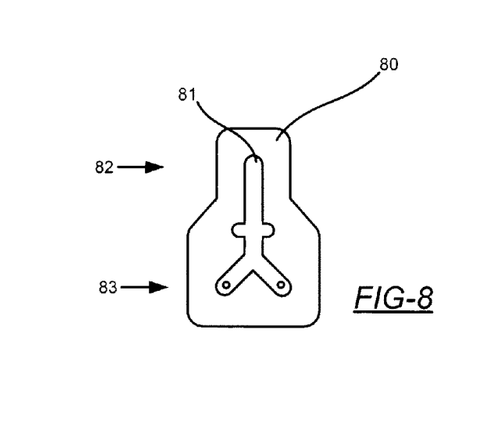
FIG. 8 depicts a first example of a titanium reinforced bi-layered membrane.

FIG. 8 depicts an example of a bi-layered titanium reinforced membrane which is reinforced with the titanium binder shown in FIG. 7. In this example, the bi-layered titanium reinforced membrane can have a body 80 with tapered or rounded edges which covers or encloses the titanium frame 81 on either side, such that the titanium frame 81 is placed within or enveloped between the layers of the membrane. The body 80 of the bi-layered reinforced membrane can have a narrowed portion 82 along one end and a wider portion 83 along an opposite end, such that the narrow portion 82 and wider portion 83 substantially covers and outlines the shape of the body of the titanium frame 81. The bi-layered titanium reinforced membrane of FIG. 8 can have a textured surface and a substantially smooth surface and can comprise two layers or sheets of PTFE. A first layer or sheet comprised of unsintered high density PTFE (dPTFE) having a density of about 1.2 gm/cc to about 2.3 gm/cc (as described in U.S. Pat. No. 5,957,690) can be used to form the textured surface. A second layer or sheet which can be used to form the substantially smooth surface can be comprised of expanded PTFE (ePTFE) and have a measurable internodal distance; Table 1 provides exemplary specifications for the internodal distance and density.

TABLE 1

| | Characteristics | Value | Tolerance | Units | Sampling Plan | Level | AQL |
|---|---|---|---|---|---|---|---|
| 1 | Inside Diameter | 20.00 | +1.00/−1.50 | mm | ANSI/ASQC Z1.9 | GLII | 2.5 |
| 2 | Wall Thickness | 0.25 | ±0.04 | mm | ANSI/ASQC Z1.9 | GLII | 2.5 |
| 3 | Internodal Distance | 65.0 | ±15.0 | Microns | ANSI/ASQC Z1.9 | GLII | 4.0 |

Specifically, the d-PTFE material which may be implemented as the first layer or sheet of material forming the textured surface can be made from a high density PTFE with a density in a range of about 1.2 grams/cc to about 2.3 grams/cc; for some applications, the density of d-PTFE may be in a range of about 1.45 grams/cc to about 1.55 grams/cc. As set forth above, the d-PTFE material may be unsintered and unexpanded with a nominal pore channel size of less than about 5 micrometers. In some embodiments, the unsintered, unexpanded d-PTFE may have a nominal pore channel size of less than 2 micrometers. In some embodiments, the unsintered, unexpanded d-PTFE may have a nominal pore channel size of less than 0.5 micrometers. In some embodiments, the unsintered, unexpanded d-PTFE may have a nominal pore channel size of less than 0.2 micrometers. This small pore channel size may allow a composite multi-layer material employing d-PTFE to exhibit superior functional characteristics, resulting clinically in reduced host response (inflammation), soft tissue in-growth, and resultant adhesions.

The textured surface of the first layer or sheet of material forming the textured surface of the present invention can be made by first forming a thin sheet of unsintered PTFE and then embossing the sheet with indentations. PTFE resin is mixed with a lubricant such as mineral spirits to form a paste. The paste is then calendered between rollers to form a thin flat sheet of the desired thickness in the range of about 0.125 mm to 0.25 mm. The calendering is performed to reduce the thickness of the sheet and to impart substantially uniform strength in all directions to the sheet. The lubricant is removed by drying the sheet at temperature somewhat above the boiling point of the mineral spirit lubricant, but well below the sintering temperature of PTFE, which is about 327 degrees C. The foregoing process steps result in a flat sheet of unsintered PTFE about 0.125 to 0.25 mm thick, having a density in the range of about 1.2 gm/cc to about 2.3 gm/cc, and having substantially uniform strength in all directions. The resulting flat sheet has two substantially smooth surfaces.

After the sheet has been dried, the sheet can be embossed to form the indentations in one of its surfaces. In the certain embodiments, the embossing step can be performed by placing a sheet of patterned polymer mesh on top of the unembossed sheet of unsintered PTFE. The patterned polymer sheet material, such as polyethylene or polypropylene, is typically harder and has more compressive strength than the unsintered PTFE material. In some embodiments the polymer sheet can be a suitable commercially available fine pore-size sheet filter material. The polymer sheet can have a pattern that is embossed. The polymer sheet and the unsintered PTFE sheet can be passed together between a pair of rollers, which emboss the pattern of the polymer sheet into one surface of the unsintered PTFE sheet. After embossing, the polymer sheet may be discarded. After embossing, the embossed unsintered PTFE sheet may be cut into smaller sheets of various shape and size for formation of the titanium reinforced bi-layered membrane.

In some embodiments of the composite bi-layered titanium reinforced membrane, the sheet of unsintered, textured d-PTFE forming the first layer may be laminated or otherwise combined with the sheet of substantially smooth, expanded e-PTFE forming the second layer, to surround or envelope or at least partially surround or envelope, the titanium binder creating the titanium reinforced bi-layered membrane. The shape and size of the sheets forming the layers can vary such that each sheet is partially attached to the titanium binder. In certain embodiments, each sheet may partially cover or fully cover the titanium binder. Typically the sheets of the layers will be attached, at least partially. It will be appreciated that such attachment may be accomplished by stitching layers of material, exertion of hydraulic or other pressure, application of a biocompatible adhesive or heat, or some combination of the foregoing. One or more combinations may be used in the laminating process. The composite bi-layered titanium reinforced material constructed and operative in accordance with the present disclosure may have utility in applications related to the regeneration of soft tissue defects and surgical reconstruction of bone and skeletal defects throughout the body, including reconstruction to correct maxillofacial defects, such as alveolar defects and orbital defects.

In certain embodiments, the titanium binder can be attached at a point or at least partially attached to one the PTFE sheets forming the layers. The binder can be attached by such methods as bonding, or by adhesive or mechanical fasteners. The attachment of the titanium binder can form a patch, such that a sheet forming a first layer or a top layer can be bonded to a sheet forming a second layer, or bottom layer.

Figure 9:
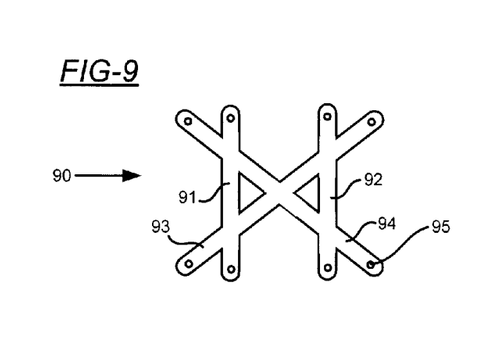
FIG. 9 depicts a second example of a titanium reinforcement binder.

FIG. 9 shows an example of a titanium reinforcement binder. The titanium reinforcement binder can have a frame 90 or body suitable for placement over a bone cavity, such as an alveolar cavity. Frame 90 in the example has a plurality of elongate members including a pair of members 91 and 92 in an X-shaped configuration with two parallel elongate members 93 and 94 traversing the frame 90. Each of the plurality of elongate members 91-94 may be provided with a perforation or pilot hole. For example, elongate member 94 has a hole 95 located at a distal end of the member 94. Holes can be used for securing the frame 90 at one or more points using a fastener, such as a surgical screw or pin, to an area of bone at a surgical site. Pilot holes can be provided based on the application and/or dimensions of the defect to be repaired. In some embodiments, a plurality of predrilled pilot holes may be provided in the frame. Pilot holes enable a surgeon to more rapidly place and attach the fastener relative to the defect.

Figure 10:
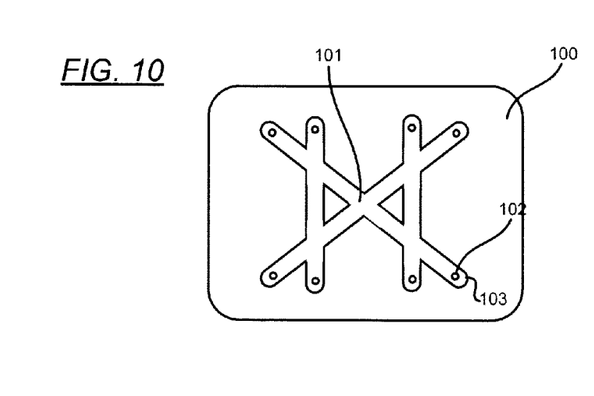
FIG. 10 depicts a second example of a titanium reinforced bi-layered membrane.

FIG. 10 shows a bi-layered titanium reinforced membrane reinforced by the titanium binder shown in FIG. 9. The bi-layered titanium reinforced membrane can have a body 100 with tapered or rounded edges which can cover or encloses the titanium frame 101 on either side, such that the titanium frame 101 can be bonded within or enveloped between the layers of the membrane. The body 100 of the bi-layered reinforced membrane can be rectangular such that it covers the titanium binder.

The bi-layered titanium reinforced membrane of FIG. 10 can have a textured surface and a substantially smooth surface and can comprise two layers or sheets of PTFE. A first layer or sheet, which may comprise unsintered high density PTFE (dPTFE) having a density of about 1.2 gm/cc to about 2.3 gm/cc (as described in U.S. Pat. No. 5,957,690), forms the textured surface. A second layer or sheet which can be used to form the substantially smooth surface is comprised of expanded PTFE (ePTFE) which has a measurable internodal distance; the internodal distance and the density are provided in the product specifications set forth in Table 1.

Specifically, the d-PTFE material which may be implemented as the first layer, or sheet of material forming the textured surface can be a high density PTFE with a density in a range of about 1.2 grams/cc to about 2.3 grams/cc; for some applications, the density of d-PTFE may be in a range of about 1.45 grams/cc to about 1.55 grams/cc. As set forth above, the d-PTFE material may be unsintered and unexpanded having a nominal pore channel size of less than about 5 micrometers. In some embodiments, the unsintered, unexpanded d-PTFE may have a nominal pore channel size of less than 2 micrometers. In some embodiments, the unsintered, unexpanded d-PTFE may have a nominal pore channel size of less than 0.5 micrometers. In some embodiments, the unsintered, unexpanded d-PTFE may have a nominal pore channel size of less than 0.2 micrometers. This small pore channel size may allow a composite multi-layer material employing d-PTFE to exhibit superior functional characteristics, resulting clinically in reduction of: host response (inflammation), soft tissue in-growth, and resultant adhesions.

In some embodiments, the textured surface of the first layer or sheet of material used to form the textured surface can be made by first forming a thin sheet of unsintered PTFE and then embossing the sheet with indentations as described above.

In accordance with some embodiments, the sheet of unsintered, textured d-PTFE which can be used to form the first layer may be laminated or otherwise combined with the sheet of substantially smooth, expanded e-PTFE which can be used to form the second layer, such that the layers surround, envelope, or at least partially attach. It will be appreciated that such attachment may be accomplished by stitching layers of material, exertion of hydraulic or other pressure, application of a biocompatible adhesive or heat, or some combination of the foregoing. One or more combinations may be used in the laminating process. The composite bi-layered titanium reinforced material constructed and operative in accordance with the present disclosure may have utility in applications related to the regeneration of soft tissue defects and surgical reconstruction of bone and skeletal defects throughout the body, including reconstruction to correct maxillofacial defects, such as alveolar defects and orbital defects.

The bilayered titanium reinforced membrane as shown in FIG. 10 can be used in the repair of larger areas of bone or skeletal defects, for example on the alveolar arch or other craniofacial defects such as those to the orbit of the eye. The unsintered, textured d-PTFE surface which can form the first layer can be placed such that it faces or is adjacent to the soft tissue, for example the gingival tissue, and the substantially expanded e-PTFE forming the second layer can be placed such that it faces, or is adjacent to the bone or skeletal area or cavity. It is contemplated that different configurations and sequences of layers may be employed in various applications. The material of the membrane has a substantially uniform strength in all directions and allows the surgeon to shape the membrane to a desired configuration for placement at the surgical site. The titanium frame 101 may also be shaped or formed by bending prior to placement at the site. The titanium binder can be made from such materials that it holds its shape when bent. The bilayered titanium reinforced membrane is placed over or about a bone cavity or, the desired surgical site with the unsintered, textured d-PTFE forming the first layer facing the soft tissue, or for example the gingival tissue, and the with the sheet of substantially smooth, expanded e-PTFE forming the second layer facing or adjacent to the bone or skeletal cavity. The titanium reinforced bilayered membrane can then be fixed or fastened to the bone by surgical pins or screws secured to the surgical site by placement through, for example the pilot hole 102, along the distal end of the elongate member 103, of the titanium frame 101.

Figure 11:
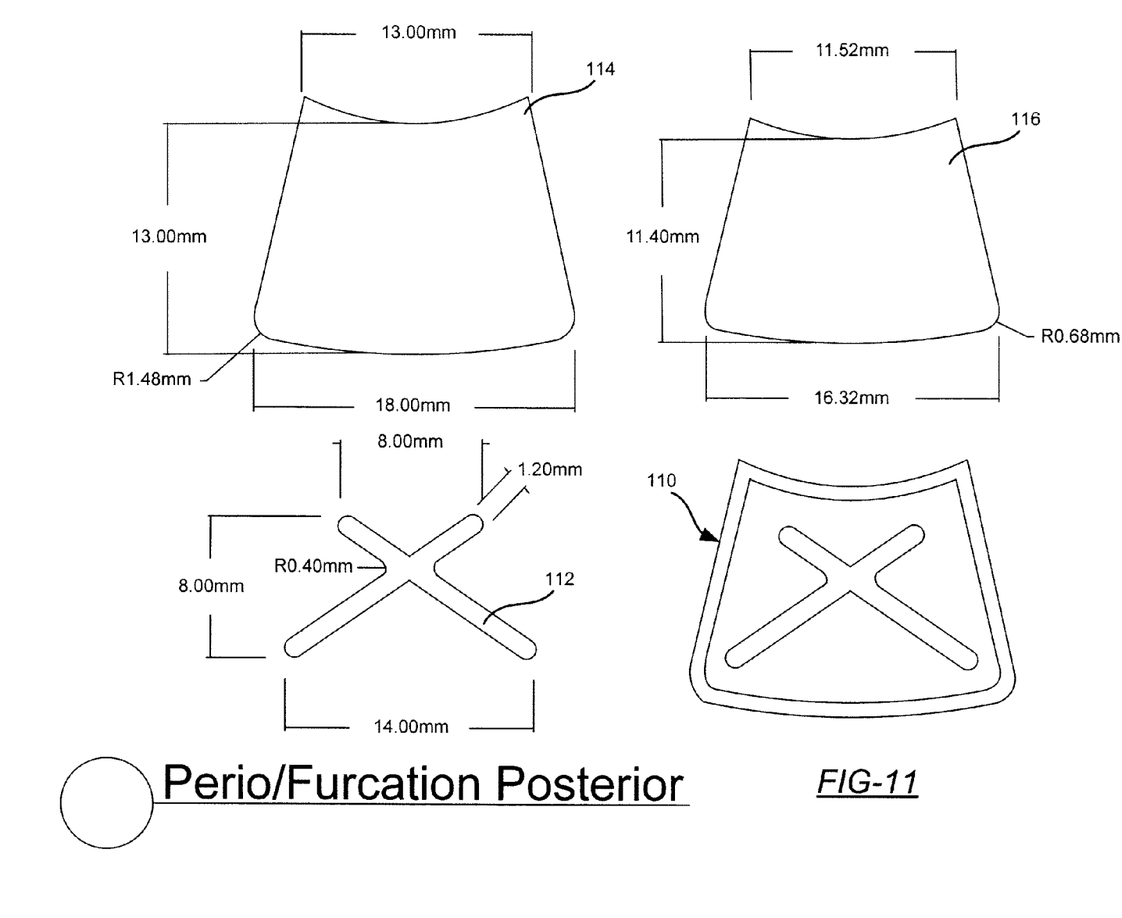
FIG. 11 depicts an assembly drawing for a third example of a reinforced bi-layered membrane.
Figure 12:
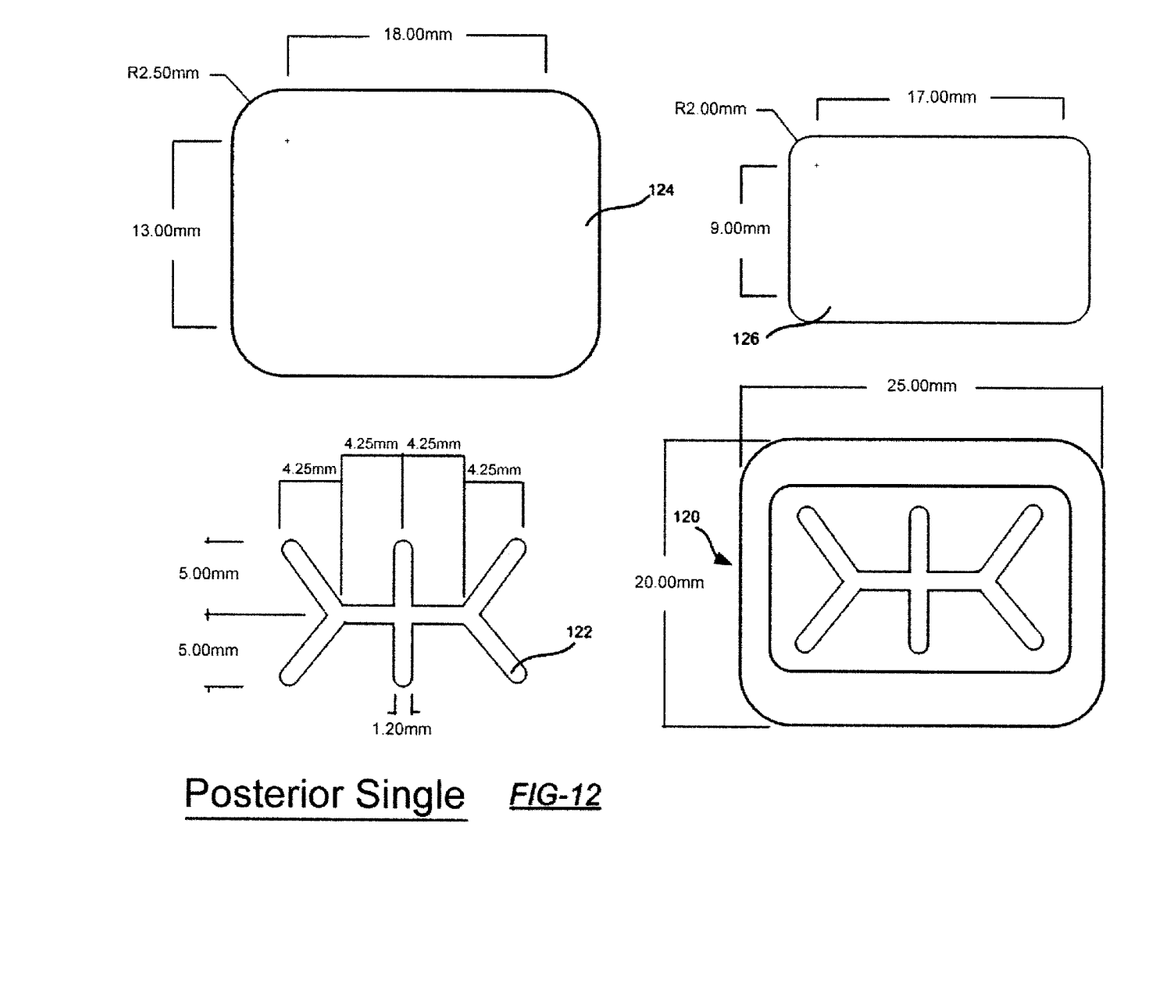
FIG. 12 depicts an assembly drawing for a fourth example of a reinforced bi-layered membrane.
Figure 13:
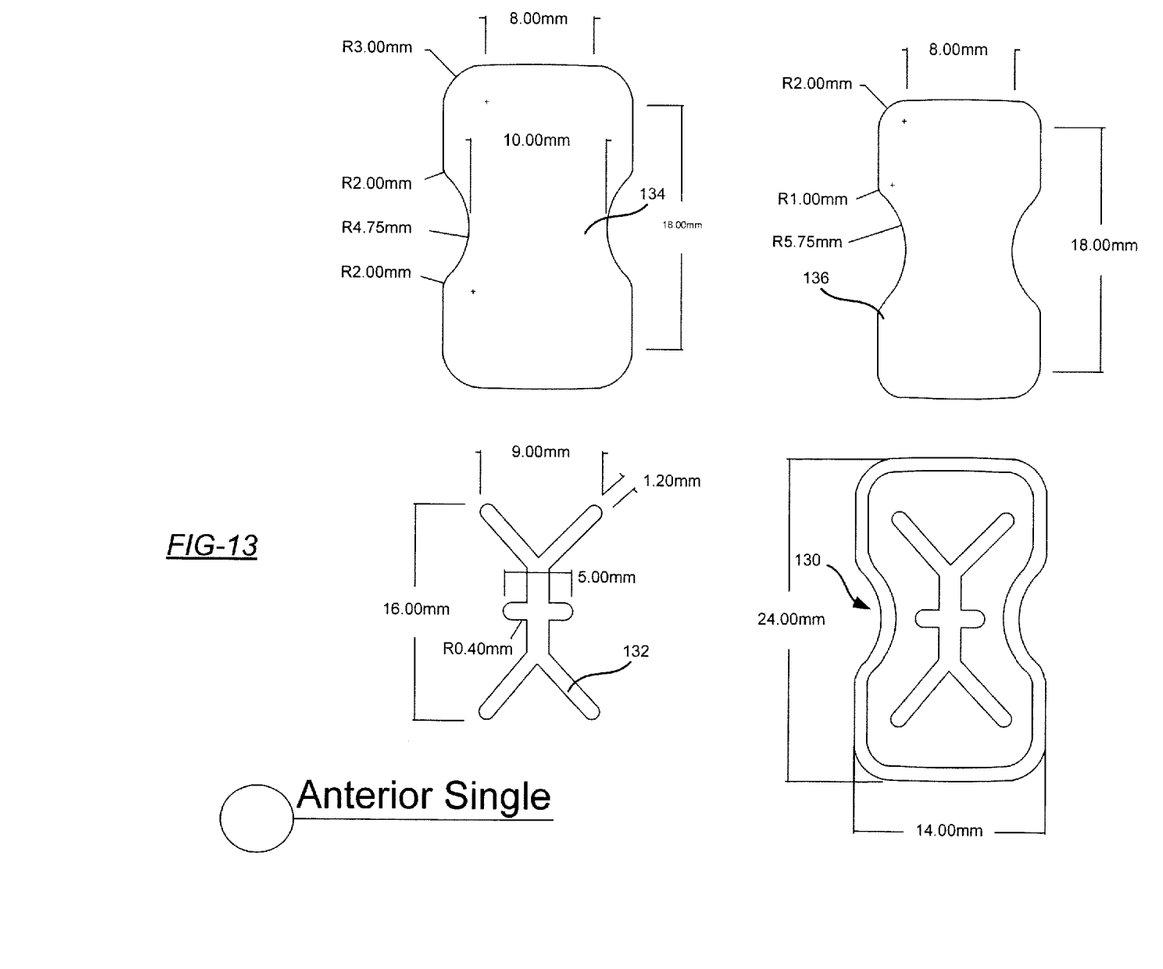
FIG. 13 depicts an assembly drawing for a fifth example of a reinforced bi-layered membrane.

FIGS. 11-13 depict components used in the manufacture of reinforced bi-layered membranes. In each of these drawings, a multilayer reinforced component 110, 120 and 130 is formed using a plurality of layers. In the examples depicted, a strength member 112, 122 and 132 is formed in a desired shape from a material suited to the application. Suitable materials can include titanium, stainless steel, composite, carbon fiber and customized micro- or nano-material based materials. First and second layers of membranes 114 and 116, 124 and 126 and 134 and 136 may be provided above, below or around strength member 112, 122 and 132. First and second layers of membranes 114 and 116, 124 and 126 and 134 and 136 may be bonded to strength member 112, 122 and 132 using adhesive and/or mechanical fasteners.

From the foregoing, it may be seen that the medical barrier of the present invention overcomes the shortcomings of the prior art, and is particularly well adapted for use in guided tissue regeneration in the repair of bone defects, as for example in the repair of alveolar bone defects. The barrier prevents the entry of rapidly migrating gingival tissue cells into the defect and allows the alveolar bone to regenerate. During healing, the gingival tissue adheres somewhat to the textured surface of the barrier to anchor the gingival tissue over the barrier, thereby preventing dehiscence or splitting open of the tissue covering the material. However, the high density unexpanded substantially non-porous nature of the medical barrier of the present invention prevents gingival tissue from growing into or through the barrier. Thus, after the bone defect has healed, the barrier may be removed with a minimum of trauma to the gingival tissue.

Additional Descriptions of Certain Aspects of the Invention

The foregoing descriptions of the invention are intended to be illustrative and not limiting. For example, those skilled in the art will appreciate that the invention can be practiced with various combinations of the functionalities and capabilities described above, and can include fewer or additional components than described above. Certain additional aspects and features of the invention are further set forth below, and can be obtained using the functionalities and components described in more detail above, as will be appreciated by those skilled in the art after being taught by the present disclosure.

Certain embodiments of the invention provide methods of repairing bone defects. Some of these embodiments comprise covering a portion of a bone defect using a reinforced membrane. Some of these embodiments comprise securing soft tissue about the membrane, whereby the membrane facilitates healing of the defect. In some of these embodiments, the membrane comprises a plurality of layers, including a binding layer and a polytetraflouroethylene polymer (PTFE) layer, the PTFE layer having a textured surface and a substantially smooth surface. In some of these embodiments, the textured surface provides a top surface of the membrane. In some of these embodiments, the substantially smooth surface contacts the bone. In some of these embodiments, the textured surface comprises unsintered PTFE. In some of these embodiments, the substantially smooth surface comprises expanded PTFE. In some of these embodiments, the binding layer comprises a titanium binder.

Some of these embodiments comprise filling the bone defect with particulate grafting material prior to placing the reinforced layered membrane. In some of these embodiments, the unsintered PTFE has a density of about 1.2 gm/cc to about 2.3 gm/cc. In some of these embodiments, the expanded PTFE has a measurable internodal distance. In some of these embodiments, the binding layer is positioned between a top and bottom PTFE layer.

Certain embodiments of the invention provide reinforced materials. Some of these embodiments comprise a titanium binder configured to span a bone cavity and adapted for fixation to bone surrounding the bone cavity. Some of these embodiments comprise a PTFE membrane attached at one or more points to the titanium binder. In some of these embodiments, the titanium binder has one or more elongate members and wherein the titanium binder may be formed to obtain a desired shape. In some of these embodiments, the elongate members have one or more predrilled holes suitable for securing a fastener to an area of bone. In some of these embodiments, the fastener is a surgical screw. In some of these embodiments, the fastener is a surgical pin. In some of these embodiments, at least one of the elongate members is free to move independently of the PTFE membrane. In some of these embodiments, the PTFE membrane is attached to a portion of a bottom layer of the PTFE membrane.

Certain embodiments of the invention provide systems, methods and devices for repairing a bone defect. Some of these embodiments comprise covering a portion of a bone defect using a membrane that includes a reinforcing member. Some of these embodiments comprise fastening the reinforcing member to an area of bone. Some of these embodiments comprise securing soft tissue about the membrane. In some of these embodiments, the membrane facilitates healing of the defect. In some of these embodiments, the membrane comprises a plurality of layers, including a binding layer and a polytetraflouroethylene polymer (PTFE) layer, the PTFE layer having a textured surface and a substantially smooth surface.

In some of these embodiments, the textured surface provides a top surface of the membrane. In some of these embodiments, the substantially smooth surface contacts the bone. In some of these embodiments, the textured surface comprises unsintered PTFE. In some of these embodiments, the unsintered PTFE has a density of between 1 gm/cc to about 4 gm/cc. In some of these embodiments, the substantially smooth surface comprises expanded PTFE. In some of these embodiments, expanded PTFE has a measurable internodal distance. In some of these embodiments, the reinforcing member is embodied in the binding layer. In some of these embodiments, the binding layer comprises a titanium binder. In some of these embodiments, the binding layer is positioned between a top and bottom PTFE layer. Some of these embodiments comprise filling the bone defect with particulate grafting material prior to covering the portion of the bone defect with the membrane.

In some of these embodiments, the plurality of layers comprise a first layer formed from unsintered, substantially unexpanded polytetrafluoroethylene polymer having no measurable, repeatable internodal distance. In some of these embodiments, the unsintered substantially unexpanded polytetrafluoroethylene polymer has a density in a range of about 1.2 gm/cc to about 2.3 gm/cc. In some of these embodiments, the unsintered substantially unexpanded polytetrafluoroethylene polymer has a plurality of pores having a nominal channel size of less than 5 micrometers. In some of these embodiments, the plurality of layers comprise a second layer formed from an open structured material. In some of these embodiments, surfaces of the first and second layers are attached at a common interface.

Although the present invention has been described with reference to specific exemplary embodiments, it will be evident to one of ordinary skill in the art that various modifications and changes may be made to these embodiments without departing from the broader spirit and scope of the invention. Accordingly, the specification and drawings are to be regarded in an illustrative rather than a restrictive sense.

What is claimed is:

1. A reinforced material comprising:
 a titanium binder configured to span a bone cavity and adapted for fixation to bone surrounding the bone cavity; and
 a polytetraflouroethylene membrane attached at one or more points to the titanium binder, wherein
 the titanium binder having multiple elongate members forming a junction, the elongate members including a first elongate member having a free distal end that extends away from the junction, wherein the titanium binder may be formed into a desired shape, wherein the first elongate member has a predrilled hole formed in the free distal end spaced apart from the junction, the predrilled hole being suitable for receiving a fastener that passes through the polytetraflouroethylene membrane and into an area of bone, and wherein the polytetraflouroethylene membrane comprises a plurality of layers, including a binding layer and a polytetraflouroethylene polymer layer, the polytetraflouroethylene polymer layer having a textured surface and a substantially smooth surface, wherein the substantially smooth surface contacts the bone and the textured surface provides a top surface.

2. The reinforced material of claim 1, wherein the fastener is a surgical screw.

3. The reinforced material of claim 1, wherein the fastener is a surgical pin.

4. The reinforced material of claim 1, wherein a portion of a top layer of the polytetraflouroethylene membrane is attached to a portion of a bottom layer of the polytetraflouroethylene membrane.

5. The reinforced material of claim 1, wherein the fastener is operative for fastening the titanium binder to bone.

6. The reinforced material of claim 1, wherein the textured surface comprises unsintered polytetraflouroethylene.

7. The reinforced material of claim 1, wherein the unsintered polytetraflouroethylene has a density of about 1.2 gm/cc to about 2.3 gm/cc.

8. The reinforced material of claim 1, wherein the substantially smooth surface comprises expanded polytetraflouroethylene.

9. The reinforced material of claim 8, wherein the expanded polytetraflouroethylene has a measurable internodal distance.

10. The reinforced material of claim 1, wherein a reinforcing member is disposed within the binding layer.

11. The reinforced material of claim 1, wherein the binding layer is positioned between a top polytetraflouroethylene layer and a bottom polytetraflouroethylene layer.

12. The reinforced material of claim 1, wherein the elongate members include a second elongate member having a second free distal end that extends away from the junction, and wherein second elongate member has a second predrilled hole suitable formed in the second free distal end spaced apart from the junction, the second predrilled hole being suitable for receiving a second fastener that passes through the polytetraflouroethylene membrane and into an area of bone.

13. The reinforced material of claim 12, wherein the elongate members include a third elongate member having a third free distal end that extends away from the junction, and wherein third elongate member has a predrilled hole formed in the third free distal end spaced apart from the junction, the third predrilled hole being suitable for receiving a second fastener that passes through the polytetraflouroethylene membrane and into an area of bone.

14. A reinforced material comprising:
a titanium binder configured to span a bone cavity and adapted for fixation to bone surrounding the bone cavity; and
a first polytetraflouroethylene membrane disposed on one side of the titanium binder, the first polytetraflouroethylene membrane being attached at one or more points to the titanium binder,
a second polytetraflouroethylene membrane disposed on a side of the titanium binder opposite the first polytetraflouroethylene membrane, the second polytetraflouroethylene membrane being attached at one or more points to the titanium binder,
wherein the titanium binder has one or more elongate members disposed between the first and second polytetraflouroethylene membranes, and wherein the titanium binder may be formed into a desired shape such that at least one of the elongate members is free to move independently of the first and second polytetraflouroethylene membranes in between the first and second polytetraflouroethylene membranes.

\* \* \* \* \*